United States Patent
Abusleme et al.

(10) Patent No.: US 10,745,555 B2
(45) Date of Patent: Aug. 18, 2020

(54) PROCESS FOR MANUFACTURING POROUS MEMBRANES

(75) Inventors: Julio A. Abusleme, Saronno (IT); Anna Maria Bertasa, Cesate (IT); Regis Faig, Baverans (FR); Marco Miele, Cisliano (IT); Stefano Mortara, Arconate (IT)

(73) Assignee: SOLVAY SPECIALTY POLYMER ITALY S.P.A., Bollate (MI) (IT)

( * ) Notice: Subject to any disclaimer, the term of this patent is extended or adjusted under 35 U.S.C. 154(b) by 0 days.

(21) Appl. No.: 14/127,101

(22) PCT Filed: Jun. 15, 2012

(86) PCT No.: PCT/EP2012/061422
§ 371 (c)(1),
(2), (4) Date: Dec. 17, 2013

(87) PCT Pub. No.: WO2012/175416
PCT Pub. Date: Dec. 27, 2012

(65) Prior Publication Data
US 2014/0131268 A1 May 15, 2014

(30) Foreign Application Priority Data
Jun. 23, 2011 (EP) ..................... 11305798

(51) Int. Cl.
| | | |
|---|---|---|
| *C08L 71/02* | (2006.01) | |
| *B01D 71/32* | (2006.01) | |
| *H01M 2/16* | (2006.01) | |
| *C08L 27/16* | (2006.01) | |
| *A61M 1/34* | (2006.01) | |
| *H01M 10/0525* | (2010.01) | |
| *C08J 5/18* | (2006.01) | |
| *C08L 27/20* | (2006.01) | |
| *C08F 214/22* | (2006.01) | |

(52) U.S. Cl.
CPC ............ *C08L 71/02* (2013.01); *A61M 1/34* (2013.01); *A61M 1/3403* (2014.02); *B01D 71/32* (2013.01); *C08J 5/18* (2013.01); *C08L 27/16* (2013.01); *C08L 27/20* (2013.01); *H01M 2/1653* (2013.01); *H01M 10/0525* (2013.01); *C08F 214/22* (2013.01); *C08J 2327/16* (2013.01); *C08J 2333/02* (2013.01); *C08J 2371/02* (2013.01)

(58) Field of Classification Search
CPC .. B01D 71/34; B01D 69/02; B01D 2321/168; B01D 2323/02; B01D 2325/36; B01D 67/0016; B01D 71/32; B01D 71/36
USPC ....................... 210/500.35, 500.36
See application file for complete search history.

(56) References Cited

U.S. PATENT DOCUMENTS

| | | | |
|---|---|---|---|
| 4,702,836 A | 10/1987 | Mutoh et al. | |
| 4,772,440 A * | 9/1988 | Kasi ................... | B01D 67/0016 210/500.36 |
| 4,774,132 A | 9/1988 | Joffee et al. | |
| 4,964,990 A * | 10/1990 | Kraus ................ | B01D 67/0011 210/490 |

(Continued)

FOREIGN PATENT DOCUMENTS

| | | |
|---|---|---|
| EP | 276957 A2 | 8/1988 |
| EP | 1236503 A1 | 9/2002 |

(Continued)

OTHER PUBLICATIONS

Deng et al, "microporous polymer electrolyte based on PVDF/PEO star polymer blends for lithium ion batteries", Jounal of M. Science 491 (215) 82-89.*

(Continued)

*Primary Examiner* — Ana M Fortuna

(57) ABSTRACT

The present invention pertains to a process for the manufacture of a porous membrane, said process comprising the following steps: (i) providing a composition [composition (F)] comprising: —at least one fluoropolymer [polymer (F)] comprising recurring units derived from at least one (meth) acrylic monomer (MA) having formula (I) wherein: —$R_1$, $R_2$ and $R_3$, equal to or different from each other, are independently selected from a hydrogen atom and a $C_1$-$C_3$ hydrocarbon group, and —$R_X$ is a hydrogen atom or a $C_1$-$C_5$ hydrocarbon moiety comprising at least one functional group selected from a hydroxyl, a carboxyl, an epoxide, an ester and an ether group, and —at least one poly(alkylene oxide) (PAO); (ii) processing said composition (F) to provide a film; (iii) treating the film so obtained with an aqueous composition to provide said porous membrane. The present invention also relates to films and compositions used in said process, to porous membranes obtained from said process and to use of said porous membranes as separators in Lithium-ion batteries, as filtration membranes or in biomedical applications.

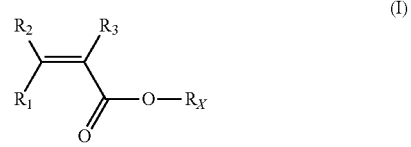

(I)

15 Claims, No Drawings

(56) References Cited

U.S. PATENT DOCUMENTS

| | | | | |
|---|---|---|---|---|
| 5,108,607 A * | 4/1992 | Kraus | ................ | B01D 67/0011 210/500.39 |
| 5,198,162 A * | 3/1993 | Park | ................ | C08J 9/26 264/41 |
| 5,834,107 A * | 11/1998 | Wang | ................ | B01D 39/083 210/490 |
| 6,060,530 A | 5/2000 | Chaouk et al. | | |
| 6,107,393 A * | 8/2000 | Abusleme | ................ | C08F 210/02 524/545 |
| 6,193,077 B1 * | 2/2001 | Witham | ................ | B01D 67/0088 210/490 |
| 6,559,192 B2 * | 5/2003 | Maccone | ................ | B01D 67/003 210/500.42 |
| 6,811,696 B2 * | 11/2004 | Wang | ................ | B01D 19/0031 210/500.22 |
| 7,455,772 B2 * | 11/2008 | Tada | ................ | B01D 67/0011 210/500.23 |
| 7,632,439 B2 * | 12/2009 | Mullette | ................ | B01D 67/0018 210/500.23 |
| 7,909,178 B2 * | 3/2011 | Ishiodori | ................ | B01D 69/02 210/500.23 |
| 2003/0215710 A1 * | 11/2003 | Lavoie | ................ | B29C 47/0004 429/212 |
| 2004/0047095 A1 * | 3/2004 | Reynolds | ................ | G06F 1/26 361/62 |
| 2006/0047095 A1 | 3/2006 | Pacetti | | |
| 2008/0034972 A1 * | 2/2008 | Gough | ................ | A61B 5/14532 96/4 |
| 2009/0188857 A1 * | 7/2009 | Moore | ................ | B01D 53/228 210/500.34 |
| 2011/0207841 A1 * | 8/2011 | Kosar | ................ | B01D 71/34 521/134 |
| 2014/0131268 A1 * | 5/2014 | Abusleme | ................ | B01D 71/32 210/321.6 |
| 2014/0378569 A1 * | 12/2014 | Abusleme | ................ | C08G 18/7621 521/145 |
| 2015/0129496 A1 * | 5/2015 | Sanguineti | ................ | B01D 69/12 210/640 |
| 2015/0140473 A1 * | 5/2015 | Abusleme | ................ | H01M 8/1023 429/516 |
| 2017/0253760 A1 * | 9/2017 | Zheng | ................ | C09D 127/16 |

FOREIGN PATENT DOCUMENTS

| | | | |
|---|---|---|---|
| EP | 1621573 A1 | | 2/2006 |
| JP | 08302135 A | | 11/1996 |
| KR | 2012-045797 | * | 4/2012 |
| WO | 9634051 A2 | | 10/1996 |
| WO | 2003068374 A1 | | 8/2003 |
| WO | 2008129041 A1 | | 10/2008 |
| WO | 2009091351 A2 | | 7/2009 |
| WO | 2011015517 A1 | | 2/2011 |

OTHER PUBLICATIONS

Xiao et al, Macroporous polymer electrolytes based on PVDF/PEO-b-PMMA block copolymer blends for rechargeable lithium ion battery, Journal of membrane science 334 (2009) 117-122.*

"Van De Ven T.G.M. et al., ""PEO-induced flocculation of fines: effects of PEO dissolution conditions and shear history"", Colloids and Surfaces A: Physicochemical and Engineering Aspects, Nov. 9, 2004, vol. 248, Issues 1-3, pp. 151-156—Elsevier B.V."

Xiao Q. et al., "Macroporous polymer electrolytes based on PVDF/PEO-b-PMMA block copolymer blends for rechargeable lithium ion battery", Journal of Membrane Science, May 15, 2009, vol. 334, No. 1-2, pp. 117-122, XP026035739, ISSN: 0376-7388, DOI: 10.1016/J.MEMSCI.2009.02.018 [retrieved on Mar. 4, 2009]—Elsevier, Amsterdam, NL.

* cited by examiner

PROCESS FOR MANUFACTURING POROUS MEMBRANES

This application is a U.S. national stage entry under 35 U.S.C. § 371 of International Application No. PCT/EP2012/061422 filed Jun. 15, 2012, which claims priority to European Application No. 11305798.8, filed Jun. 23, 2011. The entire contents of these applications are explicitly incorporated herein by this reference.

TECHNICAL FIELD

The present invention pertains to a process for the manufacture of porous fluoropolymer based membranes, to films and compositions used in said process, to porous membranes obtained from said process and to use of said porous membranes as separators in Lithium-ion batteries, as filtration membranes or in biomedical applications.

BACKGROUND ART

Porous membranes based on fluoropolymers are known in the art which are endowed with outstanding chemical, thermal and mechanical resistance.

Among frequently used methods for producing porous membranes of vinylidene fluoride (VDF) polymers, methods wherein the surface of the membrane is coated or cross-linked with (meth)acrylic monomers are known in the art.

For instance, U.S. Pat. No. 4,774,132 (PALL CORPORATION) 27 Sep. 1988 discloses a method for manufacturing porous membranes based on vinylidene fluoride polymers obtained by graft-polymerizing onto a polyvinylidene fluoride substrate a vinylic monomer. Preferred vinylic monomers include, notably, acrylic acid, 2-hydroxyethyl acrylate, 2-hydroxyethyl methacrylate.

Also, membranes of VDF polymers have been proposed in the past which do not require any further grafting/coating step; thus, EP 1621573 A (KUREHA CORPORATION) 1 Feb. 2006 discloses porous membranes prepared by a composition comprising a vinylidene fluoride (VDF) copolymer with 0.01-10% by moles of a monomer, said monomer having at least one group selected from an epoxy, a hydroxyl, a carboxyl, an ester, an amide and an acid anhydride group, a plasticizer and a suitable solvent. The composition so obtained is melt-extruded into a film, the film is cooled to be solidified, then subjected to extraction of the plasticizer and further stretched.

Further, WO 2008/129041 (SOLVAY SOLEXIS S.P.A.) 30 Oct. 2008 discloses porous membranes of a linear semi-crystalline VDF copolymer with 0.05-10% by moles of a (meth)acrylic monomer, wherein recurring units derived from (meth)acrylic monomers are randomly distributed throughout the whole vinylidene fluoride backbone. Commonly used processes for the manufacture of said porous membranes of VDF copolymers typically include at least one step including one of irradiation, film expansion, template leaching, solution precipitation techniques.

Membranes based on ethylene/chlorotrifluoroethylene (ECTFE) or ethylene/tetrafluoroethylene (ETFE) polymers have been also disclosed in the past.

Thus, U.S. Pat. No. 4,702,836 (ASAHI KASEI) 27 Oct. 1987 discloses porous membranes made of a fluorinated resin selected from ECTFE, ETFE and/or polychlorotrifluoroethylene (PCTFE). These membranes are obtained by melt-moulding a composition comprising the fluorinated resin, an inorganic fine powder material and a mixture of a chlorotrifluoroethylene oligomer and certain organic heat resistant substances, removing by extraction with a suitable solvent the chlorotrifluoroethylene oligomer and the organic heat resistant substance from the molded product obtained and further removing by extraction therefrom with a suitable solvent the inorganic fine powder material.

Also, WO 03/068374 (US FILTER WASTEWATER GROUP) 21 Aug. 2003 discloses porous polymeric ultrafiltration or microfiltration membranes including ECTFE and methods of production thereof wherein a mixture of ECTFE with a solvent system is heated and then rapidly cooled so that a non-equilibrium liquid-liquid phase separation occurs to form a continuous polymer rich phase and a continuous polymer lean phase, then removing the polymer lean phase from the solid polymeric material.

Finally, EP 1236503 A (AUSIMONT S.P.A.) 4 Sep. 2002 discloses porous membranes of a semi-crystalline fluoropolymer comprising (a) ethylene, (b) chlorotrifluoroethylene or tetrafluoroethylene, and (c) an hydrogenated monomer, which can be notably an acrylic monomer, such as, inter alia, acrylic acid, hydroxyethylacrylate, hydroxypropylacrylate, (hydroxy)ethylhexylacrylate. These membranes are prepared by processing a solution of said fluoropolymers with suitable plasticizers and then by extracting therefrom the plasticizer by dipping the membrane into a suitable solvent.

Nevertheless, due to certain environmental concerns, efforts are now devoted to find out methods wherein porous membranes of fluoropolymers are manufactured using alternative solvents having a more favourable toxicological profile.

There is thus still a need in the art for a process for manufacturing porous membranes based on fluoropolymers which advantageously enables obtaining porous membranes in a convenient way, while also avoiding use of polluting solvents and thus eliminating cost, safety and environmental concerns related to handling of large volume of said solvents.

SUMMARY OF INVENTION

It is thus an object of the present invention a process for the manufacture of a porous membrane, said process comprising the following steps:
(i) providing a composition [composition (F)] comprising:
   at least one fluoropolymer [polymer (F)] comprising recurring units derived from at least one (meth)acrylic monomer (MA) having formula (I) here below:

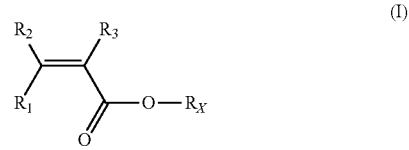

wherein:
   $R_1$, $R_2$ and $R_3$, equal to or different from each other, are independently selected from a hydrogen atom and a $C_1$-$C_3$ hydrocarbon group, and
   $R_X$ is a hydrogen atom or a $C_1$-$C_5$ hydrocarbon moiety comprising at least one functional group selected from a hydroxyl, a carboxyl, an epoxide, an ester and an ether group, and
   at least one poly(alkylene oxide) (PAO);
(ii) processing said composition (F) to provide a film;
(iii) treating the film so obtained with an aqueous composition to provide said porous membrane.

The Applicant has surprisingly found that by the process of the present invention a fluoropolymer based porous membrane is advantageously obtained, while also avoiding use of organic solvents and thus reducing costs and environmental concerns.

By the term "fluoropolymer [polymer (F)]", it is hereby intended to denote a polymer comprising recurring units derived from at least one fluorinated comonomer (F).

By the term "fluorinated comonomer [comonomer (F)]", it is hereby intended to denote an ethylenically unsaturated comonomer comprising at least one fluorine atom.

Most preferred fluorinated comonomers (F) are vinylidene fluoride (VDF), chlorotrifluoroethylene (CTFE), hexafluoropropylene (HFP), tetrafluoroethylene (TFE), trifluoroethylene (TrFE) and vinyl fluoride.

The polymer (F) of step (i) of the process of the invention may further comprise recurring units derived from at least one hydrogenated comonomer [comonomer (H)].

By the term "hydrogenated comonomer [comonomer (H)]", it is hereby intended to denote an ethylenically unsaturated comonomer free of fluorine atoms.

Non-limitative examples of suitable hydrogenated comonomers (H) include, notably, ethylene, propylene, vinyl monomers such as vinyl acetate.

For the purpose of the present invention, the term "film" is intended to denote a continuous, generally thin, sheet. By the term "continuous", it is hereby intended to denote a film free of aggregates.

For the purpose of the present invention, the term "porous membrane" is intended to denote a discrete, generally thin, interface which moderates permeation of chemical species in contact with it, said membrane containing pores, holes or voids of finite dimensions. The terms "pore", "hole" and "void" will be used as synonyms within the context of the present invention.

The porous membrane obtained from the process of the invention is advantageously a symmetrical porous membrane.

Membranes wherein the pores are randomly distributed though the thickness of the membrane are generally known as symmetrical porous membranes; membranes wherein the pores are not homogeneously distributed through the thickness and aggregates are present are generally known as asymmetrical porous membranes.

Porous membranes are generally characterized by an average pore diameter (d) and a porosity (c), said porosity being a measure of the fraction of the volume of the membrane which is porous.

The fluoropolymer [polymer (F)] of step (i) of the process of the present invention comprises typically from 0.1% to 10% by moles of recurring units derived from at least one (meth)acrylic monomer (MA) having formula (I) as described above.

The (meth)acrylic monomer (MA) preferably complies with formula (II) here below:

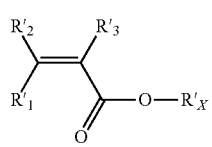
(II)

wherein:
$R'_1$, $R'_2$ and $R'_3$ are hydrogen atoms, and
$R'_X$ is a $C_1$-$C_5$ hydrocarbon moiety comprising at least one functional group selected from a hydroxyl, a carboxyl and an ester group.

The (meth)acrylic monomer (MA) more preferably complies with formula (III) here below:

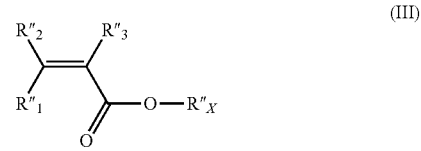
(III)

wherein:
$R''_1$, $R''_2$ and $R''_3$ are hydrogen atoms, and
$R''_X$ is a $C_1$-$C_5$ hydrocarbon moiety comprising at least one hydroxyl group.

Non-limitative examples of (meth)acrylic monomers (MA) include, notably, hydroxyethyl(meth)acrylate, hydroxypropyl(meth)acrylate, hydroxyethylhexyl(meth) acrylate.

The monomer (MA) is even more preferably selected from the followings:

hydroxyethyl acrylate (HEA) of formula:

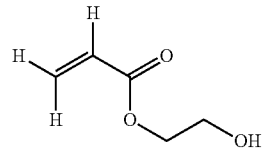

2-hydroxypropyl acrylate (HPA) of either of formulae:

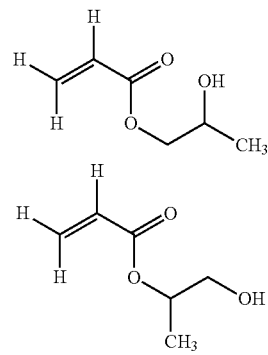

and mixtures thereof.

Very good results have been obtained when the monomer (MA) is hydroxyethyl acrylate (HEA).

According to a first embodiment of the process of the invention, the polymer (F) of step (i) of the process of the invention is a fluoropolymer [polymer ($F_1$)] comprising:
recurring units derived from vinylidene fluoride (VDF), and
recurring units derived from at least one (meth)acrylic monomer (MA) having formula (I) as described above.

The polymer ($F_1$) of step (i) of the process of the invention comprises typically at least 70% by moles, preferably at least 80%, more preferably at least 90% by moles of recurring units derived from vinylidene fluoride (VDF).

The polymer ($F_1$) of step (i) of the process of the invention comprises typically at least 0.1% by moles, preferably at least 0.2% by moles, more preferably at least 0.3% by moles of recurring units derived from at least one (meth)acrylic monomer (MA) having formula (I) as described above.

The polymer ($F_1$) of step (i) of the process of the invention comprises typically at most 10% by moles, preferably at most 3% by moles, more preferably at most 1.5% by moles of recurring units derived from at least one (meth)acrylic monomer (MA) having formula (I) as described above.

The polymer ($F_1$) of step (i) of the process of the invention may further comprise recurring units derived from at least one other fluorinated comonomer (F) as defined above.

Should another fluorinated comonomer (F) be present, the polymer ($F_1$) of step (i) of the process of the invention comprises typically from 0.1% to 10% by moles, preferably from 0.2% to 8% by moles, more preferably from 0.5% to 7.5% by moles of recurring units derived from said fluorinated comonomer (F).

The polymer ($F_1$) of step (i) of the process of the invention is preferably a fluoropolymer comprising:
from 0.3% to 1.5% by moles of recurring units derived from at least one (meth)acrylic monomer (MA) having formula (I) as described above, wherein the recurring units derived from vinylidene fluoride (VDF) are the complement to 100% by moles of total recurring units.

According to a variant of this first embodiment of the process of the invention, the polymer ($F_1$) of step (i) of the process of the invention may further comprise from 0.5% to 7.5% by moles of recurring units derived from hexafluoropropylene (HFP).

The polymer ($F_1$) of step (i) of the process of the invention is more preferably a fluoropolymer comprising:
from 0.3% to 1.5% by moles of recurring units derived from at least one (meth)acrylic monomer (MA) having formula (III) as described above, wherein the recurring units derived from vinylidene fluoride (VDF) are the complement to 100% by moles of total recurring units.

The polymer ($F_1$) of this first embodiment of step (i) of the process of the invention can be manufactured by aqueous suspension polymerization or by aqueous emulsion polymerization processes. The polymer ($F_1$) of this first embodiment of step (i) of the process of the invention is preferably manufactured by an aqueous suspension polymerization process as described in WO 2008/129041 (SOLVAY SOLEXIS S.P.A.) 30 Oct. 2008.

According to a second embodiment of the process of the invention, the polymer (F) of step (i) of the process of the invention is a fluoropolymer [polymer ($F_2$)] comprising:
recurring units derived from ethylene (E),
recurring units derived from a fluorinated comonomer (F) selected from tetrafluoroethylene (TFE), chlorotrifluoroethylene (CTFE) and mixtures thereof, and
recurring units derived from at least one (meth)acrylic monomer (MA) having formula (I) as described above.

The polymer ($F_2$) of this second embodiment of step (i) of the process of the invention comprises typically from 0.1% to 10% by moles of recurring units derived from at least one (meth)acrylic monomer (MA) having formula (I) as described above.

The polymer ($F_2$) of this second embodiment of step (i) of the process of the invention preferably has a mole ratio between ethylene (E) and fluorinated comonomer(s) (F) ranging from 10:90 to 70:30.

The polymer ($F_2$) of this second embodiment of step (i) of the process of the invention more preferably comprises:

from 35% to 65%, preferably from 45% to 55%, more preferably from 48% to 52% by moles of recurring units derived from ethylene (E),
from 65% to 35%, preferably from 55% to 45%, more preferably from 52% to 48% by moles of recurring units derived from chlorotrifluoroethylene (CTFE) and/or from tetrafluoroethylene (TFE), and
from 0.5% to 5% by moles, preferably from 1% to 3% by moles of recurring units derived from at least one (meth)acrylic monomer (MA) having formula (I) as described above.

The polymer ($F_2$) of this second embodiment of step (i) of the process of the invention is even more preferably an ECTFE polymer, that is to say that the fluorinated comonomer (F) is chlorotrifluoroethylene (CTFE).

The poly(alkylene oxide) (PAO) has a number average molecular weight typically comprised between 100000 and 5000000, preferably between 200000 and 4000000, more preferably between 300000 and 2000000.

The poly(alkylene oxide) (PAO) is more preferably a poly(ethylene oxide) (PEO) having a number average molecular weight typically comprised between 100000 and 5000000, preferably between 200000 and 4000000, more preferably between 300000 and 2000000.

It is generally understood, without this limiting the scope of the invention, that the amount of at least one poly(alkylene oxide) (PAO) used in step (i) of the process of the invention will determine the porosity (c) and the average pore diameter (d) of the porous membrane obtained by the process of the invention.

The composition (F) of step (i) of the process of the invention typically contains more than 5% by volume, preferably more than 20% by volume, more preferably more than 30% by volume, based on the total volume of the composition, of at least one poly(alkylene oxide) (PAO).

Upper boundaries for the amount of at least one poly(alkylene oxide) (PAO) are not particularly critical. It is nevertheless understood that the composition (F) will generally comprise at most 80% by volume, preferably at most 70% by volume, more preferably at most 65% by volume, based on the total volume of the composition, of at least one poly(alkylene oxide) (PAO).

The composition (F) of step (i) of the process of the invention is typically prepared by standard methods.

Usual mixing devices like static mixers, high intensity mixers can be used. High intensity mixers are preferred for obtaining better mixing efficiency.

The composition (F) of step (i) of the process of the invention is preferably a powdery composition ($F_p$) comprising at least one polymer (F) and at least one poly(alkylene oxide) (PAO) under the form of powders.

In step (ii) of the process of the invention, films can be manufactured from the composition (F) by traditional methods.

In step (ii) of the process of the invention, the composition (F) is typically processed by film extrusion. According to this technique, the composition is extruded through a die so as to obtain a molten tape, which is then calibrated and stretched in the two directions until obtaining the required thickness and wideness.

According to a preferred embodiment of step (ii) of the process of the invention, the composition (F) is melt compounded for obtaining a molten composition. Generally, melt compounding is carried out in an extruder. Composition is typically extruded through a die at temperatures of generally lower than 250° C., preferably lower than 200° C. to yield strands which are cut for providing pellets.

Twin screw extruders are preferred devices for accomplishing melt compounding of the composition (F) of the process of the invention.

Films can then be manufactured by processing the pellets so obtained through traditional film extrusion techniques. Film extrusion is preferably accomplished through a flat cast film extrusion process or a hot blown film extrusion process. Film extrusion is more preferably accomplished by a hot blown film extrusion process.

The films so obtained are advantageously continuous films of polymer (F) and poly(alkylene oxide) (PAO).

Particularly preferred films are those having a thickness of less than 250 μm, preferably of less than 200 μm, more preferably of less than 150 μm.

In step (iii) of the process of the invention, the film is treated with an aqueous composition at a temperature typically lower than 90° C., preferably lower than 75° C., more preferably lower than 65° C.

In step (iii) of the process of the invention, the film is treated with an aqueous composition typically for less than 10 hours, preferably for less than 8 hours.

The skilled in the art is aware of suitable standard techniques which will enable him to treat the film so obtained with an aqueous composition to obtain a porous membrane having the average pore diameter (d) and the porosity (ε) required.

The aqueous composition of step (iii) of the process of the invention may further comprise one or more other liquid media.

Suitable liquid media which can be used in step (iii) of the process of the invention include, notably, aliphatic alcohols, preferably having from 1 to 6 carbon atoms such as, e.g., methanol and isopropanol.

Good results have been obtained with aqueous compositions comprising water in amount of more than 50% by weight, preferably of more than 60% by weight, more preferably of more than 80% by weight.

Very good results have been obtained with aqueous compositions consisting essentially of water.

In step (iii) of the process of the invention, the film is preferably dipped in a water bath at a temperature lower than 90° C.

The Applicant thinks, without this limiting the scope of the invention, that by treatment of the film obtained by step (ii) of the process of the invention with an aqueous composition the poly(alkylene oxide) (PAO) is advantageously at least partially and even substantially completely (in certain cases) extracted from said film, leaving holes in the initial continuous structure of the dense film, so that porous membranes are successfully obtained from the process of the invention.

It is generally understood, without this limiting the scope of the invention, that the porosity (ε) of the porous membrane typically increases with increasing the amount of poly(alkylene oxide) (PAO) extracted from the film obtained by step (ii) of the process of the invention.

The skilled in the art will select appropriate process conditions in this step (iii) of the process of the invention so as to tune the fraction of at least one poly(alkylene oxide) (PAO) which may remain in the porous membrane obtained by step (iii) of the process of the invention.

The porous membrane obtained by step (iii) of the process of the invention may comprise at least one poly(alkylene oxide) (PAO) in an amount of typically less than 20% by weight, preferably less than 15% by weight, more preferably less than 10% by weight based on the total weight of said porous membrane.

The Applicant has surprisingly found that a porous membrane based on at least one polymer (F) as defined above and further comprising at least one poly(alkylene oxide) (PAO) is advantageously endowed with enhanced hydrophilic properties.

After treatment of the film obtained by step (ii) of the process of the invention with the liquid composition of step (iii) of the process of the invention, an aqueous composition is obtained which usually further comprises at least one poly(alkylene oxide) (PAO). The poly(alkylene oxide(s)) (PAOs) can be filtered from said liquid composition using known technologies (see, e.g., T. G. M., Van de Ven, et al. PEO-induced flocculation of fines: effects of PEO dissolution conditions and shear history. *Colloids and Surfaces A: Physicochem. Eng. Aspects*. 2004, vol. 248, p. 151-156.). The poly(alkylene oxide) (PAO) may thus be advantageously recovered from the process of the invention.

The porous membrane so obtained can be under the form of a flat-sheet or can be produced under the form of thin tubes or fibers (hollow-fiber membranes). Flat-sheet membranes are generally preferred when high fluxes are required. Formation of membrane into hollow fibers is particularly advantageous when compact modules with high surface areas are required.

The porous membrane obtained by step (iii) of the process of the present invention is typically recovered from the liquid composition and typically dried at a temperature generally lower than 150° C., preferably lower than 100° C. so that a dried porous membrane is obtained.

The dried porous membrane has typically an average pore diameter (d) of advantageously at least 0.01 μm, preferably of at least 0.05 μm, more preferably of at least 0.1 μm and advantageously of at most 25 μm, preferably of at most 10 μm, more preferably of at most 5 μm, even more preferably of at most 1 μm.

The dried porous membrane has typically a porosity (ε) of advantageously at least 5%, preferably at least 10% and advantageously at most 90%, preferably at most 80%.

The dried porous membrane has typically a thickness of less than 250 μm, preferably of less than 200 μm, more preferably of less than 150 μm.

Another object of the present invention is a film made of a composition comprising:
at least one fluoropolymer [polymer (F)] comprising recurring units derived from at least one (meth)acrylic monomer (MA) having formula (I) here below:

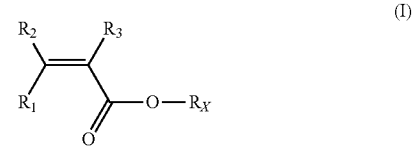

wherein:
$R_1$, $R_2$ and $R_3$, equal to or different from each other, are independently selected from a hydrogen atom and a $C_1$-$C_3$ hydrocarbon group, and
$R_X$ is a hydrogen atom or a $C_1$-$C_5$ hydrocarbon moiety comprising at least one functional group selected from a hydroxyl, a carboxyl, an epoxide, an ester and an ether group, and
at least one poly(alkylene oxide) (PAO).

The fluoropolymer [polymer (F)] and the poly(alkylene oxide) (PAO) of the film of the present invention are defined as above.

The film of the present invention is preferably made of a composition consisting of:
- at least one fluoropolymer [polymer (F)] comprising recurring units derived from at least one (meth)acrylic monomer (MA) having formula (I) as described above, and
- at least one poly(alkylene oxide) (PAO).

The film of the present invention is advantageously obtained according to step (ii) of the process of the invention by processing the composition (F) of step (i) of the process of the invention.

Also, another object of the present invention is a porous membrane made from the film of the present invention.

The porous membrane of the present invention is advantageously obtained according to step (iii) of the process of the invention.

Further, another object of the present invention is a porous membrane comprising:
- at least one fluoropolymer [polymer (F)] comprising recurring units derived from at least one (meth)acrylic monomer (MA) having formula (I) here below:

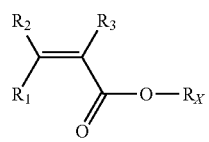

wherein:
- $R_1$, $R_2$ and $R_3$, equal to or different from each other, are independently selected from a hydrogen atom and a $C_1$-$C_3$ hydrocarbon group, and
- $R_X$ is a hydrogen atom or a $C_1$-$C_5$ hydrocarbon moiety comprising at least one functional group selected from a hydroxyl, a carboxyl, an epoxide, an ester and an ether group, and
- at least one poly(alkylene oxide) (PAO) in an amount of less than 20% by weight, preferably less than 15% by weight, more preferably less than 10% by weight based on the total weight of said porous membrane.

The fluoropolymer [polymer (F)] and the poly(alkylene oxide) (PAO) of the porous membrane of the present invention are defined as above.

The porous membrane of the present invention preferably consists of:
- at least one fluoropolymer [polymer (F)] comprising recurring units derived from at least one (meth)acrylic monomer (MA) having formula (I) as described above, and
- at least one poly(alkylene oxide) (PAO) in an amount of less than 20% by weight, preferably less than 15% by weight, more preferably less than 10% by weight based on the total weight of said porous membrane.

The porous membrane of the present invention is advantageously obtained according to step (iii) of the process of the invention.

Further, another object of the present invention is a composition comprising:
- at least one fluoropolymer [polymer (F)] comprising recurring units derived from at least one (meth)acrylic monomer (MA) having formula (I) here below:

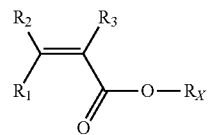

wherein:
- $R_1$, $R_2$ and $R_3$, equal to or different from each other, are independently selected from a hydrogen atom and a $C_1$-$C_3$ hydrocarbon group, and
- $R_X$ is a hydrogen atom or a $C_1$-$C_5$ hydrocarbon moiety comprising at least one functional group selected from a hydroxyl, a carboxyl, an epoxide, an ester and an ether group, and
- at least one poly(alkylene oxide) (PAO).

The fluoropolymer [polymer (F)] and the poly(alkylene oxide) (PAO) of the composition of the present invention are defined as above.

The composition of the present invention is advantageously the composition (F) of step (i) of the process of the invention.

Still, another object of the present invention is use of porous membranes of the invention as separators in Lithium-ion batteries.

Non-limitative examples of porous membranes suitable for use as separators in Lithium-ion batteries include, notably, those having a thickness of less than 50 µm, preferably of less than 25 µm.

Porous membranes made of a composition as defined above, wherein the polymer (F) is a polymer ($F_1$) as defined above, have been found to be particularly suitable for use as separators in Lithium-ion batteries.

Still, a further object of the present invention is use of porous membranes of the invention as filtration membranes such as microfiltration and ultrafiltration membranes, in particular of aqueous media, and in biomedical applications, e.g. for haemodialysis, for controlled release of drugs, for artificial organs, such as kidney, lung and pancreas.

Porous membranes made of a composition as defined above, wherein the polymer (F) is a polymer ($F_2$) as defined above, have been found to be particularly suitable for use as filtration membranes and in biomedical applications.

Should the disclosure of any patents, patent applications, and publications which are incorporated herein by reference conflict with the description of the present application to the extent that it may render a term unclear, the present description shall take precedence.

The invention will be now described in more detail with reference to the following examples whose purpose is merely illustrative and not limitative of the scope of the invention.

Raw Materials

VDF/HEA polymer having a melt flow index of 9.3 g/10 min as measured according to ASTM D1238 (190° C., 5 Kg).

VDF/HFP/HEA polymer prepared as described below and having a melt flow index of 4.3 g/10 min as measured according to ASTM D1238 (190° C., 5 Kg).

SOLEF® 21510 VDF/HFP polymer having a melt flow index of 2.3 g/10 min as measured according to ASTM D1238 (190° C., 5 Kg).

SOLEF® 6008 VDF homopolymer having a melt flow index of 8.5 g/10 min as measured according to ASTM D1238 (190° C., 5 Kg).

PEO-1: poly(ethylene oxide) having a number average molecular weight comprised between 600000 and 800000.

PEO-2: poly(ethylene oxide) having a number average molecular weight comprised between 1000000 and 1200000.

PEO-3: poly(ethylene oxide) having a number average molecular weight of about 400000.

Determination of Porosity

Porosity [% by volume] of a dried porous membrane was measured according to the following equation:

$$Porosity = \frac{\left(\frac{X[g]}{1,13 \text{ g/l}}\right)}{\left[\frac{\text{weight of the film }[g]\cdot}{\left[\left(\frac{Y[\% \text{ wt.}]}{1,13 \text{ g/l}}\right) + \left(\frac{(1-Y[\% \text{ wt.}])}{1,78 \text{ g/l}}\right)\right]}\right]} \cdot 100$$

wherein:
X represents the amount of poly(alkylene oxide) (PAO) extracted from the film, and
Y represents the weight percentage of poly(alkylene oxide) (PAO) in the film.

Determination of Ionic Conductivity

Films of polymers were dipped in an electrolyte solution of $LiPF_6$ 1 M in ethylene carbonate/propylene carbonate (1:1 weight ratio) and stored at room temperature in a dry glove-box for 24 hours. The resulting polymer electrolyte was put between two stainless steel electrodes and sealed in a container.

The resistance of the polymer electrolyte was measured and the ionic conductivity ($[\sigma]$) was calculated using the following equation:

$$[\sigma] = \frac{d}{(R_b \times S)}$$

wherein d is the thickness of the film, $R_b$ is the bulk resistance and S is the area of the stainless steel electrode.

Preparation of VDF/HFP/HEA Polymer

In a 4 lt. reactor equipped with an impeller running at a speed of 880 rpm were introduced in sequence 2410 g of demineralized water and 0.723 g of METHOCEL® K100 GR suspending agent.

The reactor was vented and pressurized with nitrogen to 1 bar, then 8.1 g of a 75% by volume solution of t-amyl perpivalate initiator in isododecane were introduced into the reactor, followed by 323 g of HFP monomer and 882 g of VDF monomer. The reactor was then gradually heated to 55° C. to a final pressure of 110 bar. Temperature was maintained constant at 55° C. throughout the whole trial. Pressure was maintained constant at 110 bar throughout the whole trial by feeding a 13.28 g/l aqueous solution of HEA monomer to a total of 682 ml. After 372 minutes the polymerization run was stopped by degassing the suspension until reaching atmospheric pressure. The polymer so obtained was then recovered, washed with demineralised water and oven-dried at 50° C. (825 g).

The polymer so obtained contained 6.6% by moles of HFP and 0.5% by moles of HEA, as determined by NMR.

General Procedure for the Manufacture of Films

Powder Mixing and Granulation

A polymer and a poly(alkylene oxide) (PAO) were blended under the form of powders and mixed in a rapid mixer equipped with a three stages paddles mixer so as to obtain a homogeneous powder mixture having the required volume ratio.

The mixture was stirred at 300 rpm for 3 minutes and then processed by extrusion in a LEISTRITZ LSM 30/34 twin-screw extruder, equipped with 6 temperature zones and a 4 mm-2 holes die. The set of temperatures in the extruder run from 140° C. to 180° C. The extruded strands were cooled in air, dried and cut in a pelletizer.

Films were manufactured from the pellets so obtained either by flat cast film extrusion or by hot blown film extrusion.

Flat Cast Film Extrusion

Pellets were processed in a single screw Braebender extruder (screw speed=25 rpm) equipped with 5 temperature zones maintained at 210° C. and a 0.5 mm×100 mm tape die. Upon exit from the die, the molten tape was rolled onto two subsequent chill rolls kept at a temperature of 115° C., whose speed was adapted so as to obtain a film thickness of about 50 µm.

Hot Blown Film Extrusion

Pellets were processed in a single screw Dr. Collin GmbH extruder having a diameter of 30 mm and a L/D of 28. The extruder was equipped with 5 heating zones, set as detailed in Table 1 here below, and an annular die having an external diameter of 51.5 mm and a gap of 0.25 mm, the die having 4 heating zones maintained at 225° C.

TABLE 1

| Feed zone | T1 | T2 | T3 | T4 | Pipe |
| --- | --- | --- | --- | --- | --- |
| 35° C. | 180° C. | 190° C. | 200° C. | 210° C. | 210° C. |

The extruder speed was set at 20 rpm and the line speed was adjusted to obtain the desired thickness of the film. The melt temperature was 214° C. The blown-up ratio was controlled by bubble internal air pressure. Upon extrusion, the bubble was collapsed in a converging frame, cooled by means of cold rollers and wound.

EXAMPLE 1—BLEND VDF/HFP/HEA POLYMER/PEO-1 (50:50 VOLUME RATIO)

A film having a thickness of 50 µm was prepared by flat cast film extrusion from a 50:50 by volume mixture of VDF/HFP/HEA polymer and PEO-1, said mixture having a melt flow index of 13.0 g/10 min, as measured according to ASTM D1238 at 190° C. under a load of 5 Kg.

A sample of 2.29 g taken from the film so obtained was placed in a 0.5 lt. water bath held at 60° C. for about 6 hours. A porous membrane was thus obtained which was recovered from said bath and dried at 70° C.

The weight percentage of poly(ethylene oxide) in the untreated film was 38.5% and the amount of poly(ethylene oxide) extracted from the film was 0.73 g.

The dried porous membrane so obtained had a porosity of 41%, as measured according to procedure as detailed hereinabove, and contained 9.6% by weight of PEO-1.

EXAMPLE 2—BLEND VDF/HEA POLYMER/PEO-2 (50:50 VOLUME RATIO)

A film having a thickness of 50 µm was prepared by flat cast film extrusion from a 50:50 by volume mixture of VDF/HEA polymer and PEO-2, said mixture having a melt flow index of 11.0 g/10 min, as measured according to ASTM D1238 at 190° C. under a load of 5 Kg.

The same procedure as detailed in Example 1 was then followed but using a sample of 1.98 g taken from the film so obtained.

The weight percentage of poly(ethylene oxide) in the untreated film was 38.5% and the amount of poly(ethylene oxide) extracted from the film was 0.74 g.

The dried porous membrane so obtained had a degree of porosity of 48%, as measured according to procedure as detailed hereinabove, and contained 1.8% by weight of PEO-2.

EXAMPLE 3—BLEND VDF/HEA POLYMER/PEO-2 (60:40 VOLUME RATIO)

A film having a thickness of 20 μm was prepared by hot blown film extrusion from a 60:40 by volume mixture of VDF/HEA polymer and PEO-2.

A sample of 6.5 g taken from the film so obtained was placed in a 5 lt. water bath held at 25° C. for about 6 hours. A porous membrane was thus obtained which was recovered from said bath and dried at 70° C.

The weight percentage of poly(ethylene oxide) in the untreated film was 29.7% and the amount of poly(ethylene oxide) extracted from the film was 1.92 g.

The dried porous membrane so obtained had a porosity of 40%, as measured according to procedure as detailed hereinabove, and contained 0.2% by weight of PEO-2. The dried porous membrane had an ionic conductivity of $1.25 \times 10^{-4}$ S/cm.

COMPARATIVE EXAMPLE 1—BLEND SOLEF® 6008 VDF HOMOPOLYMER/PEO-2 (50:50 VOLUME RATIO)

A film having a thickness of 50 μm was prepared by flat cast film extrusion from a 50:50 by volume mixture of SOLEF® 6008 VDF homopolymer and PEO-2, said mixture having a melt flow index of 2.2 g/10 min, as measured according to ASTM D1238 at 190° C. under a load of 5 Kg. The same procedure as detailed in Example 1 was then followed but an asymmetrical porous membrane was obtained where aggregates were present.

EXAMPLE 4—BLEND VDF/HFP/HEA POLYMER/PEO-3 (50:50 VOLUME RATIO)

A film having a thickness of 200 μm was prepared by flat cast film extrusion from a 50:50 by volume mixture of VDF/HFP/HEA polymer and PEO-3.

The same procedure as detailed in Example 1 was then followed but using a sample of 2.4 g taken from the film so obtained.

The weight percentage of poly(ethylene oxide) in the untreated film was 38.5% and the amount of poly(ethylene oxide) extracted from the film was 0.82 g.

The dried porous membrane so obtained had a porosity of 44%, as measured according to procedure as detailed hereinabove, and contained 6.6% by weight of PEO-3.

COMPARATIVE EXAMPLE 2—BLEND SOLEF® 21510 VDF/HFP POLYMER/PEO-3 (50:50 VOLUME RATIO)

A film having a thickness of 200 μm was prepared by flat cast film extrusion from a 50:50 by volume mixture of SOLEF® 21510 VDF/HFP polymer and PEO-3.

The same procedure as detailed in Example 1 was then followed but an asymmetrical porous membrane was obtained where aggregates were present.

It has been thus demonstrated that symmetrical porous membranes were successfully obtained from the process of the invention as notably embodied by Examples 1 to 4 according to the invention as compared with membranes obtained from comparative Examples 1 and 2 wherein aggregates were present.

The invention claimed is:

1. A process for the manufacture of a symmetrical porous membrane, said process comprising:
   processing a composition (F) by extrusion to provide a film, wherein composition (F) comprises:
   at least one fluoropolymer [polymer (F)] comprising recurring units derived from at least one (meth)acrylic monomer (MA) of formula (I):

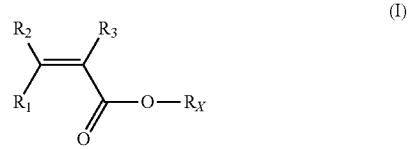

(I)

wherein:
$R_1$, $R_2$ and $R_3$, equal to or different from each other, are independently selected from a hydrogen atom and a $C_1$-$C_3$ hydrocarbon group, and
$R_X$ is a hydrogen atom or a $C_1$-$C_5$ hydrocarbon moiety comprising at least one functional group selected from a hydroxyl, a carboxyl, an epoxide, an ester and an ether group, and
greater than 30% by volume, based on the total volume of the composition, of at least one poly(alkylene oxide) (PAO);
wherein composition (F) is a powdery composition ($F_p$) comprising the at least one polymer (F) and the at least one poly(alkylene oxide) (PAO) both in the form of powders; and
treating the film so obtained with an aqueous composition to provide said porous membrane, wherein said porous membrane comprises greater than 0% by weight of the at least one poly(alkylene oxide) (PAO).

2. The process according to claim 1, wherein polymer (F) comprises from 0.1% to 10% by moles of recurring units derived from at least one (meth)acrylic monomer (MA) of formula (I).

3. The process according to claim 1, wherein the (meth)acrylic monomer (MA) complies with formula (III):

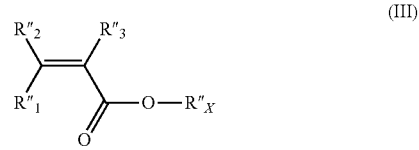

(III)

wherein:
$R''_1$, $R''_2$ and $R''_3$ are hydrogen atoms, and
$R''_X$ is a $C_1$-$C_5$ hydrocarbon moiety comprising at least one hydroxyl group.

4. The process according to claim 1, wherein the polymer (F) is a fluoropolymer [polymer ($F_1$)] comprising:

recurring units derived from vinylidene fluoride (VDF), and recurring units derived from at least one (meth)acrylic monomer (MA) of formula (I).

5. The process according to claim 1, wherein the polymer (F) is a fluoropolymer [polymer ($F_2$)] comprising:
recurring units derived from ethylene (E),
recurring units derived from a fluorinated comonomer (F) selected from tetrafluoroethylene (TFE), chlorotrifluoroethylene (CTFE) and mixtures thereof, and
recurring units derived from at least one (meth)acrylic monomer (MA) of formula (I).

6. The process according to claim 1, wherein the poly(alkylene oxide) (PAO) has a number average molecular weight comprised between 100000 and 5000000.

7. The process according to claim 6, wherein the poly(alkylene oxide) (PAO) is poly(ethylene oxide) (PEO).

8. The process according to claim 1, wherein the composition (F) contains at most 80% by volume, based on the total volume of the composition, of at least one poly(alkylene oxide) (PAO).

9. The process according to claim 1, wherein the poly(alkylene oxide) (PAO) has a number average molecular weight comprised between 200000 and 4000000.

10. The process according to claim 1, wherein the poly(alkylene oxide) (PAO) has a number average molecular weight comprised between 300000 and 2000000.

11. A symmetrical porous membrane comprising:
at least one fluoropolymer [polymer ($F_1$)] or at least one fluoropolymer [polymer ($F_2$)], or mixtures thereof wherein:
polymer ($F_1$) comprises:
recurring units derived from vinylidene fluoride (VDF), and
recurring units derived from at least one (meth)acrylic monomer (MA) of formula (I); and
polymer ($F_2$) comprises:
recurring units derived from ethylene (E),
recurring units derived from a fluorinated comonomer (F) selected from tetrafluoroethylene (TFE), chlorotrifluoroethylene (CTFE) and mixtures thereof, and
recurring units derived from at least one (meth)acrylic monomer (MA) of formula (I);
and wherein the (meth)acrylic monomer (MA) of formula (I) is:

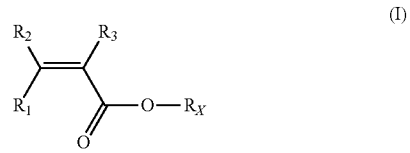

wherein:
$R_1$, $R_2$ and $R_3$, equal to or different from each other, are independently selected from a hydrogen atom and a $C_1$-$C_3$ hydrocarbon group, and
$R_X$ is a hydrogen atom or a $C_1$-$C_5$ hydrocarbon moiety comprising at least one functional group selected from a hydroxyl, a carboxyl, an epoxide, an ester and an ether group, and
at least one poly(alkylene oxide) (PAO) in an amount of greater than 0% by weight and less than 20% by weight, based on the weight of said porous membrane.

12. A lithium ion battery comprising a separator, wherein the separator comprises the porous membrane according to claim 11.

13. A biomedical device comprising a filtration membrane, wherein the filtration membrane comprises the porous membrane according to claim 11.

14. A filtration membrane comprising the porous membrane according to claim 11.

15. The porous membrane of claim 11, wherein the at least one poly(alkylene oxide) (PAO) is present in an amount of greater than 0% by weight and less than 10% by weight, based on the weight of said porous membrane.

* * * * *